US010914521B2

(12) United States Patent
Bernard et al.

(10) Patent No.: US 10,914,521 B2
(45) Date of Patent: Feb. 9, 2021

(54) SYSTEM AND METHOD FOR DRYING AND ANALYTICAL TESTING OF CONTAINERS

(71) Applicant: Versum Materials US, LLC, Tempe, AZ (US)

(72) Inventors: Matthew David Bernard, Tempe, AZ (US); Wayne Thomas McDermott, Tempe, AZ (US); Allison Barbeau Hopkins, Tempe, AZ (US); Joseph J. Siemer, Tempe, AZ (US); Michael Altschul Pingitore, Tempe, AZ (US)

(73) Assignee: Versum Materials US, LLC, Tempe, AZ (US)

( * ) Notice: Subject to any disclaimer, the term of this patent is extended or adjusted under 35 U.S.C. 154(b) by 0 days.

(21) Appl. No.: 16/255,923

(22) Filed: Jan. 24, 2019

(65) Prior Publication Data
US 2020/0240709 A1    Jul. 30, 2020

(51) Int. Cl.
*F26B 25/22* (2006.01)
*F26B 3/00* (2006.01)
*G01N 15/06* (2006.01)
*G01N 33/00* (2006.01)

(52) U.S. Cl.
CPC ............... *F26B 25/22* (2013.01); *F26B 3/00* (2013.01); *G01N 15/06* (2013.01); *G01N 33/0036* (2013.01)

(58) Field of Classification Search
CPC . F26B 25/22; F26B 25/00; F26B 3/00; G01N 15/06; G01N 33/036
USPC ........................................................ 34/437
See application file for complete search history.

(56) References Cited

U.S. PATENT DOCUMENTS

| | | | | |
|---|---|---|---|---|
| 1,525,131 A * | 2/1925 | Hitchcock | ............. | F26B 21/006 34/441 |
| 5,249,369 A * | 10/1993 | Mallet | .................. | F26B 21/008 34/104 |
| 5,513,446 A * | 5/1996 | Neubauer | ................. | F26B 5/04 34/104 |
| 6,018,885 A * | 2/2000 | Hill | ........................ | D06F 58/10 34/202 |
| 6,345,452 B1 * | 2/2002 | Feuilloley | ............. | F26B 21/006 34/437 |
| 7,186,374 B2 * | 3/2007 | Zelina | ..................... | A61L 2/186 422/1 |
| 8,595,950 B2 * | 12/2013 | Hubbard, Jr. | ............ | B01D 1/18 210/465 |
| 8,617,352 B2 * | 12/2013 | Dong | ..................... | B23K 1/008 156/345.1 |
| 10,352,333 B2 * | 7/2019 | Okada | .................. | F26B 21/006 |

(Continued)

FOREIGN PATENT DOCUMENTS

JP        2006064416 A        9/2006

*Primary Examiner* — Stephen M Gravini
(74) *Attorney, Agent, or Firm* — Lina Yang

(57) ABSTRACT

Embodiments of the present invention provide a system and method to perform drying and testing of organometallic and organosilane precursor source ampoules that have been cleaned for re-use. The drying and quality control testing is performed in a single location with a single apparatus requiring only one manual connection/disconnection step of the ampoule to the apparatus. The testing includes analyses for residual moisture, entrained particulate matter, differential pressure, and helium leak checking.

19 Claims, 8 Drawing Sheets

(56) References Cited

U.S. PATENT DOCUMENTS

| | | | |
|---|---|---|---|
| 2012/0103857 A1* | 5/2012 | Behm | C23C 16/448 |
| | | | 206/524.3 |
| 2013/0125928 A1 | 5/2013 | Cull | |
| 2018/0099872 A1 | 4/2018 | Ritter et al. | |

* cited by examiner

SYSTEM AND METHOD FOR DRYING AND ANALYTICAL TESTING OF CONTAINERS

BACKGROUND

Embodiments described herein generally relate to a method and apparatus for drying and testing a precursor source canister, also known as an ampoule, used for providing a precursor material such as an organometallic and organosilane compounds, to a processing chamber. The ampoule is capable of providing a liquid precursor material and/or a vaporized solid precursor material to the processing chamber. The ampoules are periodically taken out of service for cleaning before being dried and returned to service.

Chemical vapor deposition (CVD) and atomic layer deposition (ALD) are known techniques for forming a layer or layers of a material on a substrate, such as a semiconductor wafer. The material is generally formed by the reaction of vapor phase chemicals on and/or near the surface of the substrate. Embodiments of, CVD and ALD processes involve the delivery of gaseous reactants to the substrate surface where a chemical reaction takes place under temperature and pressure conditions favorable to the thermodynamics of the reaction The gaseous reactants, or precursors, may originate from either a liquid precursor material or a solid precursor material, either of which may be contained in the source canister or ampoule. Generally, the liquid precursor material is provided to the processing chamber by a vaporizer, which generates a vapor phase precursor from the liquid precursor material and delivers the vapor phase material to the processing chamber. Solid precursor materials are heated inside the ampoule and pressure controlled to sublimate the solid precursor material into a vapor phase precursor material, which is delivered to the processing chamber using a carrier gas. Various canisters or ampoules, for example stainless steel ampoules, are commercially available for delivery of precursors to the substrate surface.

Precursor source ampoules are used in a manufacturing process for a period of time and then returned to the precursor chemical supplier for cleaning and preparation for re-use. The ampoules are received by the supplier containing residual product and reaction and/or degradation products. Any significant amount of such residual materials is removed through a recovery process. The ampoules are then passed through a cleaning process to remove all remaining product and other contaminants.

Following this cleaning process, the ampoules are clean on a molecular level but retain significant amounts of liquid water, physisorbed water and chemisorbed water on all internal surfaces and within elastomeric valve seats. This residual water remains as a result of the cleaning process. Many organometallic compounds are highly reactive with water to form undesirable reaction products, including undesirable solid and particulate contaminants. Such solids can adversely affect ampoule performance by clogging the ampoule valves and the transfer lines leading from the ampoule to the customer point of use. Therefore, an effective and reliable means for removing residual air from and drying an ampoule before putting it back into service is critically important. Standardized quality control testing of ampoules for cleanliness and performance criteria is also desirable.

Prior art drying systems include the installation of ampoules in convection ovens that heat the entire ampoule environment. The drying systems can heat the ampoule environment only to a temperature that is limited by the maximum temperature that can be tolerated by the valve seat or other temperature-sensitive components. The convection oven systems are separate from the cleaning system and make it practical to include enhancements to the process such as longer drying times, pressure cycling of a high purity inert gas stream, and moisture analysis of the ampoule effluent high purity inert gas stream.

Prior to being returned to service, some prior art dried ampoules have been leak checked using inert gas leak detector stations and manual point testing methods. Ampoules must be removed from the drying station and moved to another physical area or shipped to a separate location, to be leak tested. Leak checking methods include "inboard" leak checking with inert gas-flooded plastic bags or similar manually installed enclosures surrounding the ampoules. An inboard inert gas leak, as used herein, refers to the infiltration of inert gas into the ampoule, such as through fittings or connections. Leak checking methods also include leak testing through ampoule valves using a stepwise valve actuation procedure.

Manual leak testing of the above type requires considerable labor and ampoule handling by operators. The leak checking methods require multiple connection and disconnection steps that may damage the ampoules, contaminate ports through ambient exposure, and introduce errors in sealing connection points. In particular, high-integrity mechanical seals can be damaged during the connection and disconnection process by deformation, scratching and embedding of foreign particles in the sealing surfaces. Manual operations of this type are also subject to errors due to the inherent variability of test techniques implemented by different operators.

Unreliable leak test procedures can fail to find defective ampoules. Mechanically faulty ampoules can thus be put back into service leading to operational failures after being filled with the high-purity chemical, returned ampoules, quality complaints and loss of business for ampoule suppliers. Failures detected during the chemical filling process can also be avoided in a similar way. Unreliable leak test procedures can also lead to false positives for sound ampoules. Such a result leads to loss of resources through unnecessary ampoule re-work.

All the methods described above require operator actuation of manual ampoule valves during processing. This process is labor intensive and subject to error in valve operation and sequencing (i.e., failing to open or close a valve at the appropriate time in the sequence). All the methods described above are performed using manual data recording which is labor intensive, subject to error, and requires subsequent data entry into a computer database to provide traceable certificates of analysis for each ampoule at each analytical step.

Another deficiency of the prior art drying systems is the lack of a means for verifying the overall cleanliness and proper flow conductance through the ampoule components. Ampoules can be tested for their particle shedding rate and the pressure drop across the ampoule to evaluate these criteria. However, such measurements must be performed in separate particle shedding test stations and differential pressure test stations. These test stations sometimes are not located at the same facility where ampoule drying is being performed, so the ampoules must be shipped off-site.

In addition to being expensive and time-consuming due to ampoule relocation, testing the ampoules for contamination and flow conductance requires multiple connection and disconnection steps that may further damage ampoules, contaminate ports through ambient exposure, and introduce errors in sealing connection points. Ampoule users continue to demand tighter control limits on precursor purity and ampoule performance. Ampoule preparation processes must be able to meet these requirements in order to satisfy market demands for purity, reliability, efficiency, reduced costs, and high-quality products. Thus, there is an unmet need for a comprehensive, efficient, and standardized system for ampoule preparation which can meet customer requirements for product quality. The apparatus and methods for implementing such a system must provide a fully comprehensive container preparation method that will address quality concerns, while accounting for constraints on cycle time, personnel, and machine resources.

SUMMARY OF THE INVENTION

Embodiments of the present invention comprise a system and method that enables drying, analytical testing, automatic manipulation of manual valves, and leak checking stainless steel ampoules to be used or re-used for delivering organometallic, organic, organosilane, or other materials. The apparatus and methods are directed to ampoules which have been cleaned following either a prior use in operation or for first time use. The invention overcomes the limitations of the prior art methods by providing a unified apparatus that can be used to automatically perform all steps of the drying, testing, leak checking and data recording processes without having to disconnect and reconnect the ampoule from the apparatus or have an operator manually transition the ampoule between process steps.

It is an object of this invention to fully dry ampoules received from a previous cleaning, first time build, or rebuild process. Ampoules may sometimes be received with amounts of moisture greater than acceptable use in the field. This invention uses a system and process using one or more techniques; heated inert gas flushing, cycle purging, vacuum, and elevated environmental temperatures to achieve the desired dryness required for field use.

It is also an object of this invention to combine two or more analytical and leak checking processes into one integrated system. This invention enables the combination of drying with moisture analysis, particle shedding and counting, differential pressure testing, and helium leak rate testing.

It is an object of this invention to leak check one or more ampoules free of liquid chemical and free of moisture. The automation and consolidation of processes allows for a uniform, consistent process flow ensuring the ampoule is free of contaminants thereby yielding a leak rate checking environment and process that is repeatable and reproducible.

It is an object of this invention to specifically use helium for leak checking, which will provide the most sensitive medium for determining a leak rate due to its low atomic mass and its ability to be selectively detected by using a mass sensitive detector.

It is an object of this invention to record in process data of the system, analytical, and leak check data of each ampoule as a means to monitor performance, show consistency, and provide traceability. The automation of data collection and its use through input/output logic enhances the consolidated capabilities of the system allowing an integrated process that is repeatable and reproducible. The data collection also serves to provide certificates of analysis as to the dryness, particulate shedding performance, differential pressure performance, or leak rate of each ampoule.

In addition, several specific aspects of the systems and methods of the present invention are outlined below.

Aspect 1: A Method for Drying Ampoules Comprising:
(a) creating an inlet connection and an outlet connection between an amoule and a drying system, each of the inlet connection and the outlet connection providing fluid flow communication between the ampoule and the drying system;
(b) drying the ampoule;
(c) performing at least one test on the ampoule, the at least one test selected from the group consisting of a moisture test, a particle test, a differential pressure test, and an ampoule leak test;
(d) collecting quality control data using at least one sensor for each of the at least one test performed in step (c);
(e) performing steps (b) through (d) after step (a) and steps (c) and (d) after step (b);
and
(f) maintaining the inlet connection and outlet connection from step (a) through step (d).

Aspect 2: The Method of Aspect 1, Further Comprising:
(g) placing the ampoule in a sealable chamber and performing steps (b) and (c) without removing the ampoule from the sealable chamber.

Aspect 3: The Method of any of Aspects 1-2, Wherein the at Least One Test Comprises at Least Two Selected from the Group Consisting of a Moisture Test, a Particle Test, a Differential Pressure Test, and an Ampoule Leak Test.

Aspect 4: The method of Aspect 2, wherein the at least one test comprises at a moisture test, a particle test, a differential pressure test, and an ampoule leak test.

Aspect 5: The Method of any of Aspects 1-4, Wherein Step (b) Further Comprises:
(b)(i) inserting the ampoule into an ampoule drying box;
(b)(ii) providing the inlet connection in fluid flow communication with a source of heated purified purge gas;
(b)(iii) purging the ampoule with the heated purified purge gas;
(b)(iv) pressure cycling the heated purified purge gas; and
(b)(v) heating the ampoule drying box using a convective flow of heated clean dry air.

Aspect 6: The method of Aspect 5, wherein the ampoule drying box comprises a first zone and a second zone, the ampoule comprises at least one elastomeric valve seat and step (b)(v) further comprises heating the first zone to a first temperature and the second zone to a second temperature that is greater than the first temperature, wherein all of the elastomeric valve seats are located in the first zone.

Aspect 7: The Method of Aspect 5, Wherein Step (b) Further Comprises:
(b)(vi) disconnecting the fluid flow communication between the inlet connection and the source of heated purified purge gas; and
(b)(vii) placing the outlet connection in fluid flow communication with a vacuum pump;
(b)(viii) placing the inlet connection in fluid flow communication with the source of heated purified purge gas;
(b)(ix) performing step (b)(vi) simultaneously or after step (b)(vi); and
(b)(x) performing step (b)(viii) after step (b)(vii).

Aspect 8: The Method of Aspect 7, Wherein Step (b) Further Comprises:
(b)(xi) performing steps (b)(vi) through (b)(viii) at least twice.

Aspect 9: The Method of any of Aspects 1-8, Wherein the at Least One Test Comprises the Differential Pressure Test, the Differential Pressure Test Comprising the Steps of:
(c)(i) enabling fluid flow communication between the ampoule outlet and a differential pressure test analyzer; and (c)(ii) measuring a differential pressure between the ampoule outlet port and the purified purge gas supply when the ampoule outlet port is in fluid flow communication with the purified purge gas supply.

Aspect 10: The Method of any of Aspects 1-9, Wherein the at Least One Test Comprises the Ampoule Leak Test, the Ampoule Leak Test Comprising the Steps of:

(c)(i) placing the ampoule outlet port in fluid flow communication with a helium source;

(c)(ii) placing the ampoule inlet port in fluid flow communication with a helium detector; and (c)(iii) measuring a helium leak rate using the helium detector while steps (c)(i) and (c)(ii) are being performed.

Aspect 11: The Method of Aspect 10, Wherein the Ampoule Leak Test Further Comprises the Step of:

(c)(iv) flooding the ampoule drying box with helium to a concentration of at least 1 percent by volume of helium in air.

Aspect 12: The method of any of Aspects 1-11, wherein the at least one test comprises the moisture test, the moisture test is performed using at least one moisture sensor and yields a detection level of 1.2 part per billion by volume or lower.

Aspect 13: The method of any of Aspects 1-12, wherein the at least one test comprises the particle test, the particle test using at least one particle counter being sensitive to a plurality of micrometer-sized particles and utilizing a plurality of particle counter channels.

Aspect 14: A Drying System for Ampoules Comprising:

a drying box adapted to provide a sealable internal volume, to selectively enable fluid flow communication with each of a source of heated, clean dry air and a box vent, and to accommodate an ampoule having an inlet port and an outlet port within the sealable internal volume;

an inlet manifold comprising at least one inlet conduit and at least one inlet manifold valve that are adapted to selectively enable fluid flow communication between the inlet port and each of a helium leak detector and a source of purified purge gas having an in-line heater;

an outlet manifold comprising at least one outlet conduit and at least one outlet manifold valve configured to selectively enable fluid flow communication between the outlet port and each of at least one quality control analyzer, a vacuum pump, a helium source, and an outlet vent;

a quality control analyzer selected from the group consisting of a moisture analyzer, a particle analyzer, a differential pressure test analyzer, and a helium leak check analyzer;

at least one controller adapted to control the source of heated, clean dry air, the box vent, the source of purified purge gas, the in-line heater, the inlet manifold valve, the outlet manifold valve, the ampoule inlet port, the ampoule outlet port, the quality control analyzer, the vacuum pump, and the outlet vent.

Aspect 15: The system of Aspect 14, wherein the at least one controller comprises executable code adapted to perform the method of Aspect 1.

Aspect 16: The system of any of Aspects 14-15, wherein the drying box further comprises a first heating zone and a second heating zone, each having a controllable heating element, wherein the at least one controller is adapted to heat the second heating zone to a higher temperature than the first heating zone.

Aspect 17: The system of Aspect 16, wherein the first heating zone is located above the second heating zone.

Aspect 18: The system of any of Aspects 14-17, wherein the quality control analyzer is a moisture analyzer capable of measuring moisture at a concentration of 1.2 part per billion by volume.

Aspect 19: The system of any of Aspects 14-18 wherein the quality control analyzer is a particle analyzer comprising particle counters sensitive to a plurality of micrometer-sized particles and utilizing a plurality of particle counter channels.

Aspect 20: The system of any of Aspects 14-19, wherein the quality control analyzer is a moisture analyzer capable of measuring moisture at a concentration of 1.2 part per billion by volume.

DETAILED DESCRIPTION OF THE PREFERRED EMBODIMENT(S)

Figure 1:
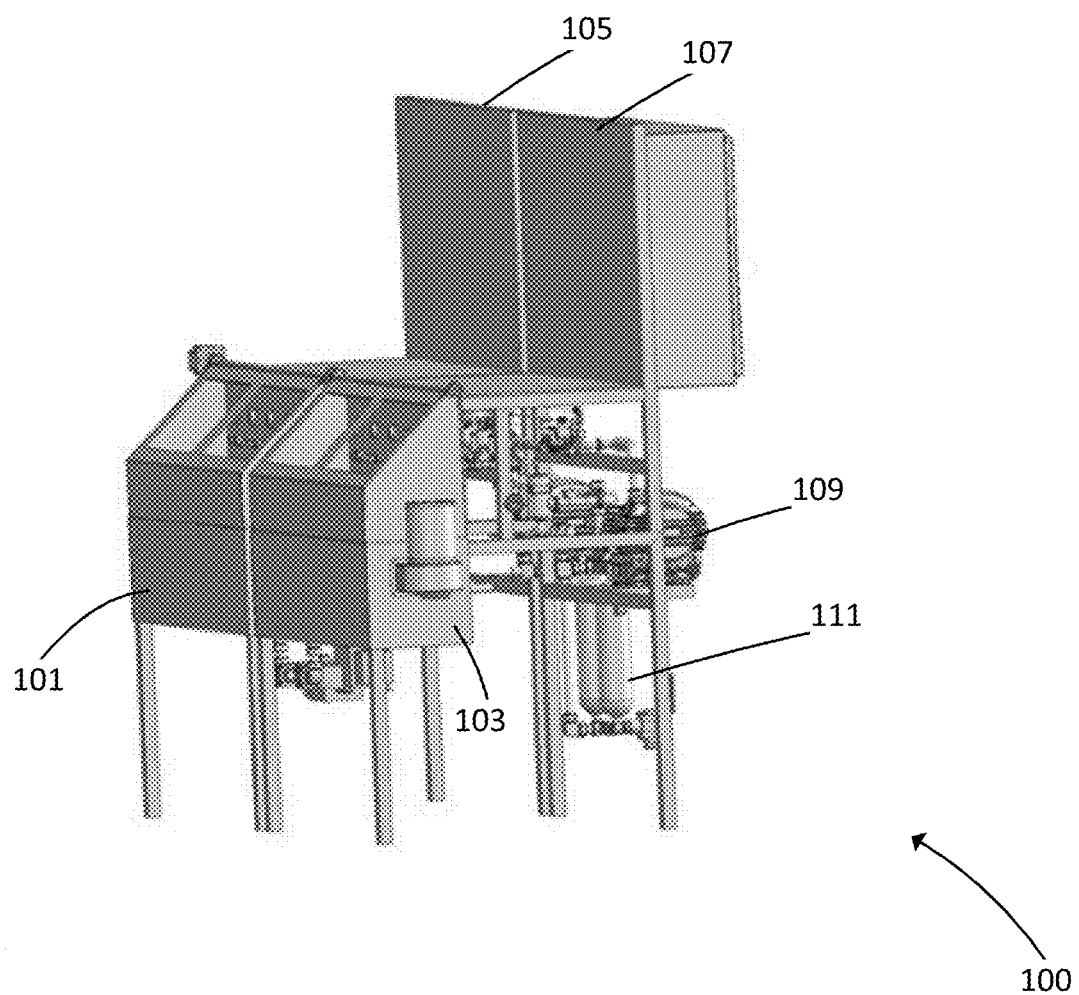
FIG. 1 is a perspective view of the ampoule drying analytical container apparatus according to an embodiment of the invention.

The ensuing detailed description provides preferred exemplary embodiments, and is not intended to limit the scope, applicability, or configuration of the invention. Rather, the ensuing detailed description of the preferred exemplary embodiments will provide those skilled in the art with an enabling description for implementing the preferred exemplary embodiments of the invention. Various changes may be made in the function and arrangement of elements without departing from the spirit and scope of the invention, as set forth in the appended claims.

For purposes of the present specification and accompanying claims, the term "fluid communication" or "fluid flow communication" each refer to the nature of connectivity between two or more components that enables liquids and/or gases to be transported between the components in a controlled fashion. Coupling, also known as connecting, two or more components such that they are in fluid communication with each other can involve any suitable method known in the art, such as with the use of, for example, piping, tubing, and/or conduits. The term "selectively" when used with the terms connected, couple of in fluid flow communication, means that there is means available for enabling and disabling the connection or coupling, such as by means of a control valve or other suitable mechanism.

Embodiments of the present invention provide an apparatus and method that performs ampoule drying and quality control testing in a single location with a single apparatus and that requires only one manual connection/disconnection step of the ampoule and the apparatus. This is contrasted to the prior art which requires multiple pieces of equipment, and multiple connection and disconnection steps, to perform the same drying, analysis, and helium leak check procedures.

According to a preferred embodiment, the apparatus and associated methods are referred to as Automated Drying Analytical Container System (ADACS). ADACS is an integrated and programmable assembly of equipment encased in a single unit that is capable of performing ampoule drying, diagnostic methods, and helium leak checking in an efficient, uniform manner.

Once an ampoule is connected to the apparatus, no further connection/disconnection steps are required to complete the drying process, as well as a suite of quality control testing procedures to include the helium leak check. In an embodiment, the apparatus is designed to process multiple ampoules simultaneously, with the drying process occurring for all ampoules simultaneously, followed by sequential ampoule quality control testing. The apparatus can be programmed to perform the drying process and quality control testing automatically and to record the testing data associated with each ampoule.

Following a suitable drying period, the ampoules are tested in place using state of the art methods. The testing includes measurement for residual moisture to low ppm or ppb levels. Testing is performed for entrained particulate matter to a fraction of a micrometer size to ensure the ampoule is free of contaminants. Testing of differential pressure to low torr levels ensures there are no obstructions in the ampoule's flow paths. The ampoules also undergo strict helium leak checking to ensure atmospheric contaminants cannot enter the ampoules after re-filling. All the above processes are performed with reliability and repeatability using a standardized apparatus and method. An integrated apparatus allows the drying and testing procedures to be performed without making multiple connection and disconnection steps which can damage ampoule fittings, introduce ambient contaminants into the ampoule, and increase the risk of error in the testing process.

The drying and testing processes are improved by being automated to minimize error, bias in sampling, and operator handling of the ampoules. Electronic data recording is used to provide an immediate database of results and a traceable certificate of analysis for each ampoule. The recorded data for each ampoule is preferably tied to a unique identifier of each ampoule.

The Ampoules

Embodiments of the present invention may be used to dry and test ampoules as described below. Ampoules, typically having a stainless steel or other metallic alloy construction, are used to contain various solid and liquid organometallic or organosilane precursors for the semiconductors, photovoltaics, optics, displays and electronics industries. Numerous variations of the materials of construction and design type are commonly used. Ampoules of this type are described in U.S. Pat. Nos. 6,526,824 and 7,124,913, the disclosures of which are incorporated by reference herein.

The ampoule preferably has one or more of the following features: manual packless (e.g. with a bellows- or diaphragm-type closure) valves in the manifold assembly; automatic (pneumatically actuated) packless valves in the manifold assembly; a bypass in the manifold assembly containing a (preferably) automatic valve; a level sensor (for liquid products); a fill port; a bolted or welded top; elastomer valve seats (also referred to herein as elastomer valve seals); a bubbler tube or inlet tube (for liquid products); a base containing a generally open volume for holding the product solid or product liquid. The diaphragm-type valves preferably are constructed from materials including, but not limited to polyimide (for example Vesper), polychlorotrifluoroethylene (PCTFE, for example, Kel-F™), perfluoroalkoxy alkanes (PFA®), or other elastomer seats, with stainless steel or other corrosion-resistant diaphragms.

The solid and liquid products which may be contained in such ampoules include but are not limited to: Tetrakis (dimethylamino)titanium (TDMAT); Tantalum Dimethylamide (PDMAT); Dicarbonylcyclopentadienyl Cobalt [CpCo(CO)2]; Dicobalt hexacarbonyl t-butylacetylene (CCTBA) and Tantalum (V) Chloride (TaCl4).

High purity inert gas, such as nitrogen or helium, may be passed through the ampoule as a product carrier during operation. High purity inert gases include, but are not limited to, helium, argon and nitrogen, and mixtures thereof, having less than 100 parts per million by volume (ppmv) of total impurities (impurities which would include water vapor and oxygen), preferably less than 1 ppmv, most preferably less than 0.001 ppmv of total impurities. The ampoules may also be heated during use. The heating is performed to affect the controlled sublimation or evaporation of the product, thereby providing a controlled delivery rate of product to the point of use. The heating may create undesirable reaction products or degradation of the product in the ampoule. Undesirable solid, possibly particulate, products may form from liquid products, and may become suspended in the ampoule head space and/or vent port and/or valve manifold. The solid contaminants may cause obstruction of flow paths, increased pressure drop and possible valve malfunction. These contaminants are removed during the cleaning process.

The invention can preferably be used for stainless steel ampoules of the general type described above. However, the invention can also be designed to process larger or smaller ampoules or closed-head drums with suitable increases or decreases in system component scale. The invention can be designed to process multiple ampoules simultaneously in accordance with any throughput requirement.

Automated Drying Analytical Container System (ADACS)

Figure 2:
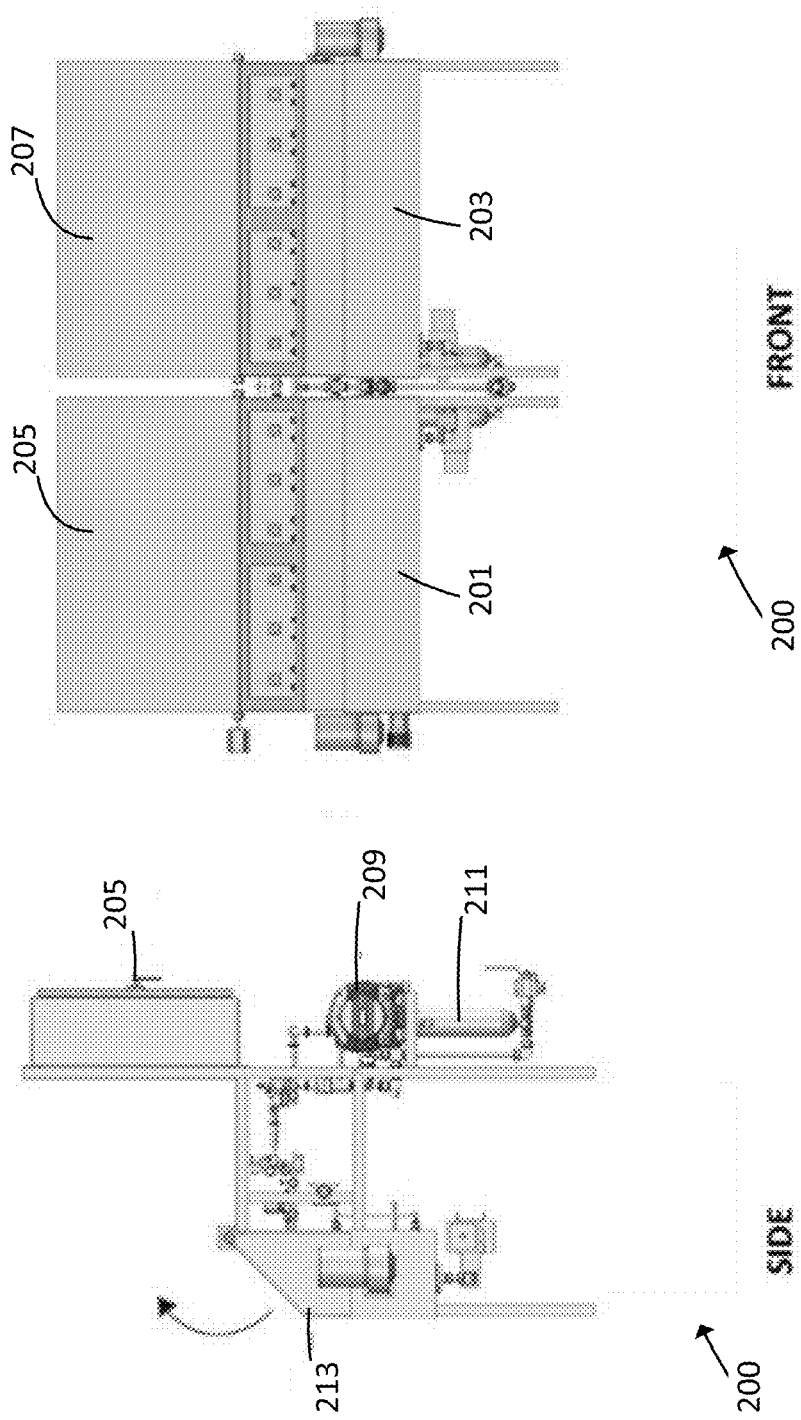
FIG. 2 is a side view and a front view of the ampoule drying analytical container apparatus according to an embodiment of the invention.

External views of an embodiment of the ADACS are provided in FIGS. 1-2. Referring to FIG. 1, an exemplary ADACS system 100, is shown. In this example, there are two banks, or drying boxes 101, 103, for enclosing six ampoules each, but other arrangements are possible. In an embodiment, the ADACS is comprised of one or more of the following components: at least one ampoule; an ampoule bank drying component; a moisture analysis component; a particle shedding analysis component; a differential pressure testing component and a leak check component. The components are integrated via a network of piping, pumps, sensors, valves and analytical instrumentation. In the illustrated embodiment, the quality control analytical instrumentation, sensors and controllers are located in instrument panels 105, 107. A vacuum pump 109 and liquid trap 111 are also mounted to the system housing.

Referring to FIG. 2, side and front views of an exemplary ADACS 200 are shown. This example has two banks, or drying box 201, 203, each accommodating up to six ampoules. Instrumentation and controllers are located in instrument panels 205, 207 located above the drying boxes 201, 203. A vacuum pump 209 and liquid trap 211 are mounted to the ADACS housing. In this embodiment, each drying box has a hinged door 213 that swings upward to allow access to the ampoules inside the drying box. Each of drying boxes 201, 203 is sealable, meaning that when the door is closed they are capable of maintaining an internal volume, surrounding the ampoules, having a controllable composition and temperature. The drying box is adapted to selectively enable fluid flow communication with each of a source of heated clean dry air and a box vent.

The system arrangement shown in FIGS. 1-2 is provided for illustrative purposes. ADACS equipment may be configured in various other arrangements according to embodiments of this invention. Such variations in equipment arrangement are designed to accommodate available space and room geometries, as well as to avoid interference with the safe operation of other nearby equipment.

Figure 3:
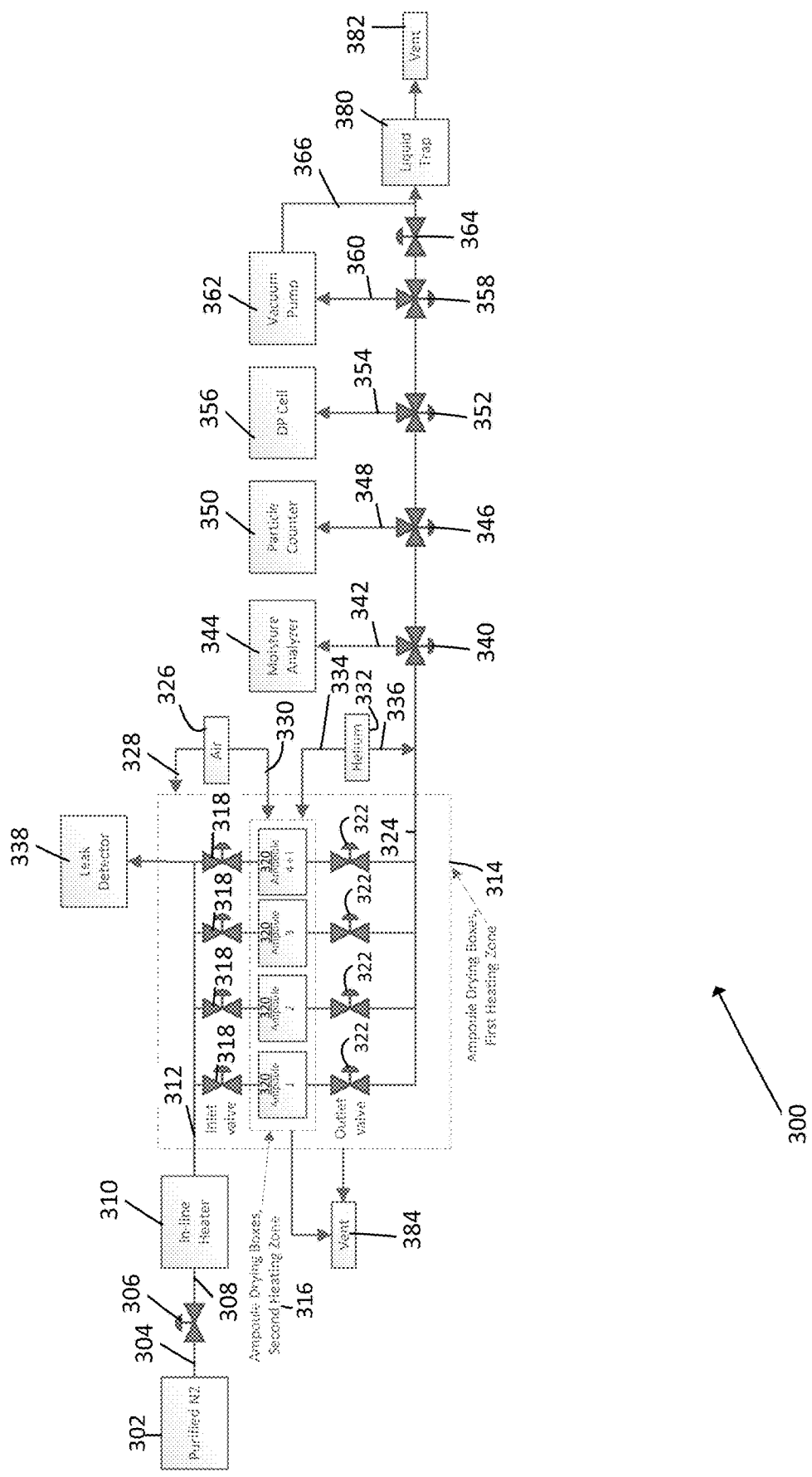
FIG. 3 is a simplified diagram of the ampoule drying analytical container apparatus according to an embodiment of the invention.

FIG. 3 shows a simplified schematic of an exemplary embodiment of the arrangement of the components of an ADACS 300. One of skill in the art will recognize the possible configurations of additional valves, conduits, controllers and electrical connections needed to complete a working system. The ADACS components are integrated with a purified inert gas supply system 302, equipped with pressure control regulators (not shown), restrictive flow orifices (not shown), and controllable in-line heaters 310 with temperature feedback circuitry (not shown). The inert gas supply system is designed to introduce heated high purity inert gas via an inlet manifold 312, also known as an influent manifold, and valves 318 into the interior of the ampoules 320 at a controlled temperature and controlled flow rate during the drying process. The inlet manifold comprises at least one inlet conduit and at least one inlet valve. In the illustrated embodiment, the inert gas is shown as nitrogen, however, any suitable inert gas, including but not limited to helium, nitrogen, neon or argon may be used. The terms purified and high purity refer to the terms used commercially to describe grades of industrial gases. An outlet manifold 324, also known as an effluent gas manifold, leading from each ampoule bank 314 comprises suitable effluent lines 324 and valves 322, 358, 364, to direct the moisture-containing effluent inert gas, produced during the drying process, to either a liquid trap-vent scrubber system 380, 382, or a vacuum pump-liquid trap-vent scrubber system 362. The outlet manifold comprises at least one outlet conduit and at least one outlet valve. A system of sample lines 342, 348, 354, 360 lead from the outlet manifold to gas sampling instrumentation, preferably one or more of a moisture analyzer 344, a particle counter 350, and a differential pressure cell 356. The valves are manipulated to selectively place one or more ampoules in fluid flow connection with the vacuum pump or quality control analyzer. In an embodiment, a controller is used to automate the manipulation of valves to provide the desired configuration for a particular drying or analysis process.

A purified helium gas supply system 332, equipped with pressure control regulators (not shown), is provided to introduce helium gas into the interior of the ampoules 320 via a conduit 336 to the outlet manifold 324 and outlet manifold valves 322. The helium can be introduced in a controlled manner through controlled sequence of manual and automatic valve actuations. The sequence of valve actuations is designed to test each ampoule individually for leakage of helium gas across each valve in its valve manifold.

The helium supply system 332, equipped with pressure control regulators (not shown), is also configured to introduce helium gas into the environment surrounding the ampoules contained in the ampoule drying box 314 via a conduit 334. A suitable ambient monitor, for example and oxygen detector (not shown) is located inside the ampoule drying box, to measure, directly or indirectly, the concentration of helium in the ampoule box. The introduction of helium gas into the ampoule drying box is designed to test each ampoule and ampoule valve manifold individually for leakage of helium gas into its evacuated interior.

A system of sample lines and valves 318 lead from the inlet side of each ampoule 320 to a helium leak detector station 338 through the inlet manifold 312 shown in FIG. 3. The helium leak detector station comprises vacuum pumps, pressure gauges, valves, and helium sensing instrumentation (not shown). The helium leak detector station is connected through the sample lines and valves 318 to each ampoule 320 individually, to measure leaks through ampoule manifold valves, or into the ampoule base or ampoule valve manifold assembly via "inboard" leaking.

A suitably programmed controller, for example, comprising intelligent devices, or multiple process logic controllers, effects control of, and/or receives input from, all system valves, heaters, fans, dampers, pressure sensors, flow sensors, liquid level sensors, compositional sensors, monitors, instrumentation, vacuum pumps, in the described systems.

The Ampoule Bank Drying Component

An effective and reliable drying process is required to remove residual water before the ampoules can be re-filled with product and re-used. Drying is performed with a combination of heating, high purity inert gas purging, and pressure cycling. The drying process allows for maximum allowable working temperatures of ampoule components, including valve seats, and level sensors. As used herein, the term pressure cycling refers to the delivery of purge gas under positive pressure until an adjustable, preselected upper pressure has been reached, at which time the pressure is allowed to decrease to an adjustable, preselected lower pressure. The sequence of alternating high and low pressure conditions is repeated for a selected number of iterations.

An embodiment comprises an automatic ampoule drying system capable of drying multiple ampoules simultaneously. Embodiments of the system, such as the ones illustrated in FIGS. 1 and 2, provide for processing up to 12 ampoules at a time in two banks of 6 ampoules 101, 103. Multiple ampoule drying boxes are provided to contain one or more of the ampoules for the purpose of drying the ampoules through external heating using forced convective flow of heated clean dry air. The drying boxes are equipped with circulating fans (not shown) to provide a well-mixed atmosphere in the environment surrounding the ampoules. The forced convective flow is provided by a source of heated, clean dry air. Clean dry air means air having a sufficiently high purity and below-ambient moisture content so as to not adversely impact the ampoule drying process. As used herein, clean dry air also includes any high purity and low moisture gas suitable for use in the drying box, including, but not limited to nitrogen.

Pivoting hoods or doors 213 are affixed to the tops or sides of each convective drying box, with the hoods designed to close over the upper valve manifolds of the contained ampoules and doors designed to close the front of the space of the contained ampoules, thereby forming a sealable enclosure for the ampoules, preferably with a resilient seal to minimize the mixing of the gas inside the hood with ambient air. A system of controllable dampers (not shown) in each drying box is capable of directing circulating air flow in a pattern to maintain a mixed atmospheric environment within each drying box, and optionally within the upper hood volume of each box.

Controllable heating elements (not shown) with temperature feedback circuitry in each drying box are capable of providing a controlled, elevated temperature in the environment surrounding the contained ampoules in the box during the drying process. The heating elements are designed to elevate the ampoule temperature sufficiently to remove residual moisture from the interior of the ampoules and ampoule manifold valve systems. In an embodiment, the maximum temperature attained in the drying box depends on the temperature limitations of the ampoule components. Optionally, the heating controls can have an independent sensor to shut off the heating elements if the internal temperature exceeds a safe setting.

In an embodiment, such as the one shown in FIG. 3, the drying box can be physically divided into two or more separate heating zones 314, 316 so that temperature-sensitive portions of the ampoules, for example the elastomeric valve seats at the top of the ampoule, can be isolated in a lower temperature zone, while the remaining portion of the ampoule can be isolated in a higher temperature zone to promote the drying process. Accordingly, in many embodiments, the lower temperature zone is preferably located above the higher temperature zone and each zone has a separately controllable heater.

The heated inert gas, vent, and vacuum pump systems are designed to operate through a controllable valve arrangement to heat, flush, and pressure cycle the ampoules sufficiently to remove residual moisture from the interior of the ampoules and ampoule manifold valve systems. A preferred high purity inert gas flow rate through each ampoule during the flushing (also known as purging) is between 0.1 and 100 standard liters per minute (slpm).

The Moisture Analysis Component

Referring to FIG. 3, a moisture check of the purge gas within each ampoule is performed using a sensitive moisture analyzer 344 after the completion of the drying process. The moisture analyzer is in fluid communication with a first sample line 342, where the first sample line is selectively in fluid communication with the effluent gas systems 324 via the actuation of a control valve 340. The moisture analyzer is preferably capable of detecting residual moisture in an inert gas stream to a detection limit below 1.2 parts per billion by volume (ppbv). Suitable monitors are well known to those skilled in the art and can include, but are not limited to, capacitive sensors, moisture-sensitive vibrating crystals and cavity ring-down spectroscopy. All ampoules 320 are purged with high purity inert gas, and remain isolated, using inlet line valves 318 and outlet line valves 322. A moisture check of the contained high purity inert gas is then performed using the moisture analyzer 344. Each ampoule is individually checked for moisture by opening the ampoule outlet line 322 to the moisture analyzer, one at a time via the outlet manifold 314. The sample gas from each ampoule 320 flows through the manifold 324 to the moisture analyzer 344. The peak moisture level measured during the sample is compared to the specification (for example, 1 ppmv). Data for each ampoule are recorded automatically by the controller (not shown). The moisture analysis procedure is described in greater detail below.

The Particle Shedding Analysis Component

A measurement of the concentration of suspended particles in the flowing high purity inert gas effluent stream is made using at least one automatic particle counter 350. Multiple measurements are possible through different ampoule flow paths depending on the ampoule configuration. The particle counter is in fluid flow communication with a second sample line 348 that is selectively in fluid communication with the outlet manifold 324 via the actuation of a control valve 346. The particle counter is preferably capable of detecting suspended particles in a high purity inert gas stream to various fractions of a micrometer in size. In an embodiment, there is a provision to impart mechanical shock to the ampoule to dislodge and enhance detection of particles from the ampoules prior to or during particle counting is optionally available. Data for each ampoule are recorded automatically by the controller (not shown).

The Differential Pressure Testing Component

The differential pressure testing is done with the differential pressure cell 356 (DP Cell). Multiple measurements are possible through different ampoule flow paths depending on the ampoule configuration. The DP Cell 356 is in fluid flow communication with a third sample line 354, that is selectively in fluid flow communication with the outlet manifold 324 via the actuation of a control valve 352. The differential pressure cell 356 is also selectively in fluid flow communication with the inlet of each ampoule (not shown). The DP cell 356 detects the difference in pressure between the inlet and outlet of each ampoule with a set flow rate of high purity inert gas flowing through the ampoule. The differential pressure cell 356 is preferably capable of detecting pressure differences as small as 1 torr at various ampoule internal pressures, gas flow rates and temperatures through an individual ampoule.

The DP Cell 356 can be used to test the differential pressure between inlet and outlet valves on each ampoule. In ampoules with a bypass line, the differential pressure through the bypass line alone can also be tested. Differential pressure data for each ampoule are recorded automatically by the controller (not shown).

The Leak Check Component

The helium leak detector 338 is selectively connected in fluid flow communication to each individual ampoule 320 via inlet manifold 312 upon the actuation of the individual ampoule's inlet valve 318. In an embodiment, the ampoules are leak checked one at a time, following the completion of the drying process and moisture, particle, and differential pressure testing processes described above. The inlet manifold 312 and inlet valves 318 are selectively controlled to open the leak detector to fluid flow communication to one ampoule at a time while the other ampoules in the bank are isolated through appropriately located valves at their inlets and outlets. A vacuum source is provided to evacuate the portions of the ampoule to verify the integrity of valve seals and to check for infiltration leaks into the ampoule. The leak check method will be described in greater detail below.

The helium leak detector process is capable of detecting leaks as small as $10^{-12}$ atm-cc/sec. Leak check data for each ampoule are recorded automatically by the controller (not shown).

Optional Additional Components

In an embodiment, the ADACS includes an automated system capable of opening and closing manually actuated valves on the valve manifolds of each ampoule in electrical communication with the controller. The automated system is capable of cycling open or closed each manual valve on each ampoule in accordance with a programmed sequence. Valve performance in opening and/or closing can be measured by through torque adjustments or torque required to reach a desired position, through measurement of degrees turned to reach a desired position, a combination of torque and degrees of rotation around a fixed axis.

Monitors designed to alert the ADACS of unsafe personnel behavior, and to direct an automatic shutdown signal to all moving parts, such as the above automatic manipulation of manually actuated valves device. Such monitors may comprise light curtains, electronic eyes, motion sensors, floor pressure pads, system sensors and the like.

An embodiment of the invention provides a means for scanning unique identifiers (i.e. bar codes, RFID tags, etc.) associated with each ampoule, and of electronically storing valve manifold configurational information, and test result data for each ampoule.

The Method of Using ADACS

Suitable standardized procedures are provided for: drying moisture-containing ampoules using heated high purity inert gas flushing combined with pressure cycling; testing the ampoules for moisture, particle shedding, and differential pressure; and checking the ampoules for minute leaks through helium leak checking in a repeatable programmed sequence.

The process flow preferably proceeds from receipt of cleaned and pre-dried ampoules, to ampoule drying, to ampoule moisture testing, to ampoule particle testing, to ampoule differential pressure testing, to ampoule leak checking. The ampoules are then passed to re-build operations for failed ampoules (not within the scope of the present invention), or to refilling of the successfully processed ampoules with high purity product (not within the scope of the present invention).

The drying steps may be repeated, as needed, if certain ampoules do not pass a previously determined moisture specification. Such failure to meet moisture specification may result from excessive moisture present in the ampoules following the cleaning and pre-drying steps (not within the scope of this invention).

Certain ampoules may fail to meet particle and/or differential pressure test specifications. Such failures may result from excessive residual contamination remaining after the cleaning steps and/or significant structural defects in the ampoules and/or manifold valves. Such problems may require re-cleaning and/or tear-down and re-building of failed ampoules.

Certain ampoules may fail to meet helium leak check specifications. Such failures may result from imperfect shut-off sealing of an ampoule's manifold valves and/or other structural defects causing measurable leakage into the ampoule's interior from the surrounding atmosphere. Such problems may require tear-down and re-building of failed ampoules.

The following steps are performed automatically using the method and apparatus of the subject invention. Preferable ADACS apparatus components and the key aspects of a typical ADACS procedures are included in this description:

Ampoule Drying

Figure 4:
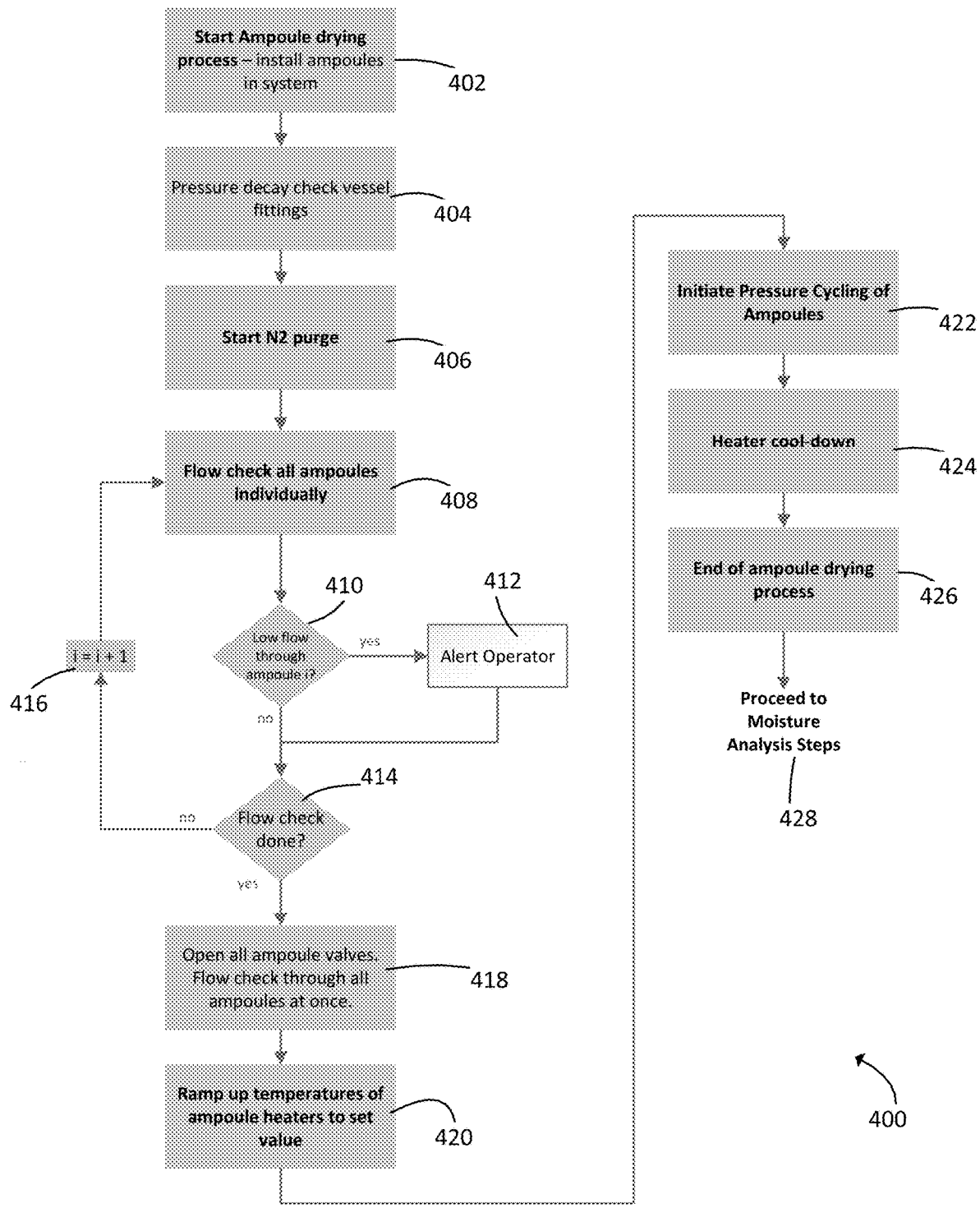
FIG. 4 is a flow chart of the ampoule drying process according to an embodiment of the invention.

FIG. 4 shows a flow diagram for the ampoule drying process 400 according to an embodiment of the invention. Ampoule drying is performed by first installing the ampoules in the apparatus of the subject invention (ADACS) 402. The installation process comprises placing each ampoule inside a drying box and creating an inlet connection and an outlet connection between the ampoule the ADACS. The docking location and design type of each installed ampoule is logged into the controller, preferably through a unique identifier of each ampoule, such as barcode scanning or RFID tags. If the design type of a specific installed ampoule is not already contained in the existing database of the unique identifier the controller can be updated to include it.

Pneumatic lines from solenoid-type pilot valves are connected to the automatic valves of all ampoules during installation. Any unused pneumatic line docking locations are capped. A manual check of all critical system components, manual valve positions and supply gas pressures is then made before the automated drying procedure is initiated. The ampoules are then checked for proper installation using a pressure decay leak check 404. Operators are alerted of any significant ampoule leak.

An initial high purity inert gas purge of all the installed ampoules simultaneously is then initiated 406. Each ampoule is then individually checked 408 to ensure inert gas flow from 0.1 to 100 standard liters per minute (slpm). Operators are notified of any significant deviation from this pre-set flow rate 410, 412. Such deviations may result from closed valves, structural defects in the ampoule/valve manifold assembly, or significant residual solid contamination obstructing flow paths through the ampoule. The flow check is repeated for each ampoule 416 until all ampoules have been checked. Once the flow check on each individual ampoule is complete 414, the valves on all the ampoules are opened simultaneously and the cumulative flow rate through all the ampoules is measured 418.

The high purity inert gas flow rate can be controlled using restrictive flow orifices, control valves, or mass flow controllers located upstream of each ampoule, and is monitored by electronic flow transducers. Other suitable flow regulating/monitoring devices, such as electronic flow controllers may also be used for this purpose.

The ampoule drying box and influent high purity inert gas stream to all ampoules are then heated to a preselected drying temperature 420. The preselected temperature is based on the tolerance of temperature sensitive components of the ampoule, usually based on component manufacturers specifications or historical knowledge from use. A preferred drying temperature range is from 50 to 250 degrees C.

Pressure cycling of the ampoules is then initiated 422. Pressure cycling is affected in the range of 0.1 torr to 7600 torr, preferably 0.5 torr to 3500 torr, more preferably 1 torr to 760 torr, in a repeatable manner for a predetermined period of time to meet operational specifications.

The heated pressure cycling is continued for the entire duration of ampoule drying. Pressure cycling is then stopped and the ampoules are cooled to ambient temperature 424. Cool-down is performed by simultaneously passing ambient temperature high purity inert purge gas through the ampoules and flowing ambient temperature air through the ampoule box. All ampoules are then pressurized to any pressure that does not exceed the maximum allowed working pressure of the ampoules. The ampoules are preferably pressurized with high purity inert gas to between 0 and 200 psig. The ampoules are then isolated using the inlet and outlet line valves. This ends the drying process 426. The ampoules remain connected to the ADACS and are now ready for the moisture analysis steps 428.

Moisture Testing

Figure 5:
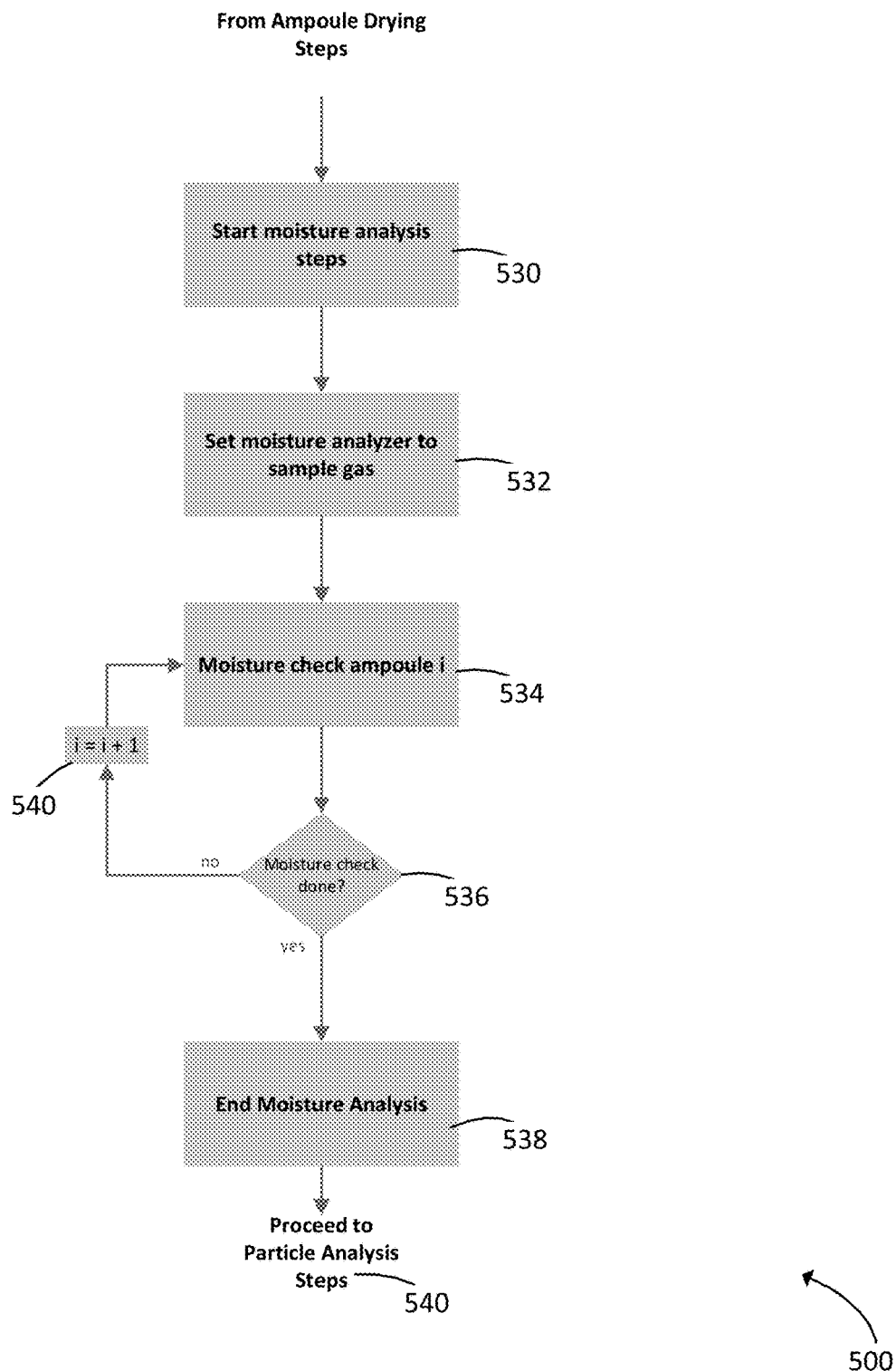
FIG. 5 is a flow chart of the ampoule moisture analysis method according to an embodiment of the invention.

FIG. 5 shows a flow diagram for the moisture testing process 500 according to an embodiment of the invention. All ampoules remain isolated under high purity inert gas pressure and at ambient or a slightly higher temperature, as they were at the conclusion of the drying process. All ampoule inlet and outlet connections to the ADACS remain connected. A moisture check of the high purity inert gas contained in each ampoule is then performed sequentially on each ampoule using a sensitive moisture analyzer 530. Each ampoule is individually checked for moisture by opening the ampoule vent lines to the moisture analyzer, one at a time 532. The sample gas from each ampoule flows through the moisture analyzer until a peak is observed 534. The peak moisture level measured during the analysis time is compared to the specification. Data for each ampoule are recorded automatically by the controller. The moisture analysis process is repeated for each ampoule installed in the ADACS 540. Once the moisture analysis has been performed on all the ampoules, the ampoules are then depressurized to 0 psig, flushed free of outgassed moisture using a high purity inert gas, and the moisture analysis is completed 538. The ampoules remain connected to the ADACS and are ready to proceed to the particle analysis steps 540.

Particle Shedding Analysis

Figure 6:
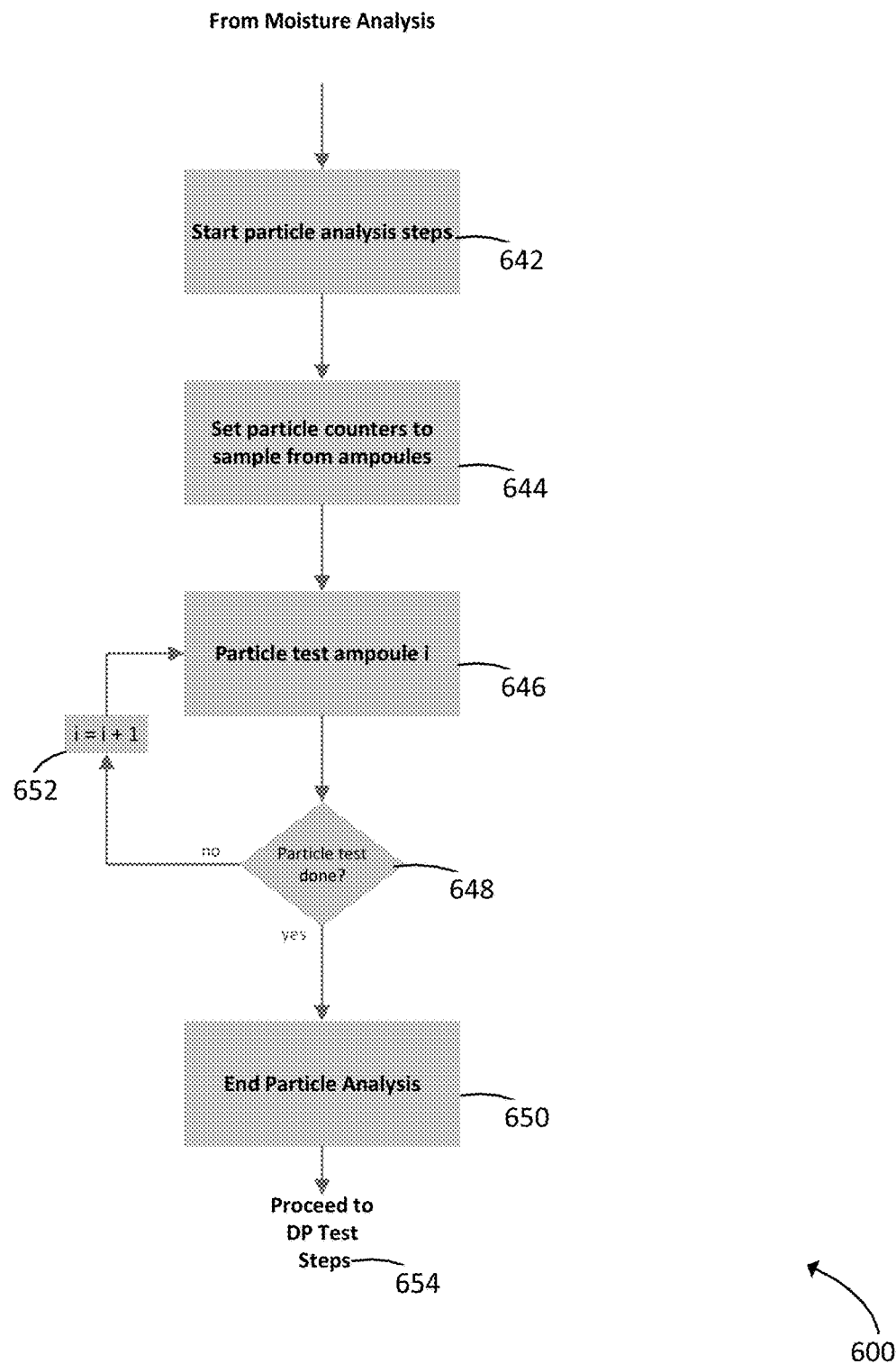
FIG. 6 is a flow chart of the ampoule particle shedding analysis method according to an embodiment of the invention.

FIG. 6 shows a flow diagram for the particle shedding analysis process 600 according to an embodiment of the invention. Ampoules are individually and sequentially tested 642 for its particle shedding rate by configuring the ADACS to connect the ampoule outlet in flow communication with the DP Cell 644. High purity inert gas is passed through each ampoule, one at a time, at a selected flow rate. Preferably the flow rate is between 0.1 and 100 slpm. A measurement of the concentration of suspended particles in the flowing inert gas effluent stream is made using at least one automatic particle counter 646. The analysis is performed for a time predetermined to be adequate for stabilized and consistent results. A preferred analysis time is between 5 and 15 minutes. The particle counter is preferably capable of detecting suspended particles in an inert gas stream to various fractions of a micrometer in size. The particle shedding analysis process is repeated for each ampoule installed in the ADACS 652. Once the particle shedding analysis has been performed on all the ampoules 648, the ampoules are ready to proceed with the differential pressure analysis.

Differential Pressure Testing

Figure 7:
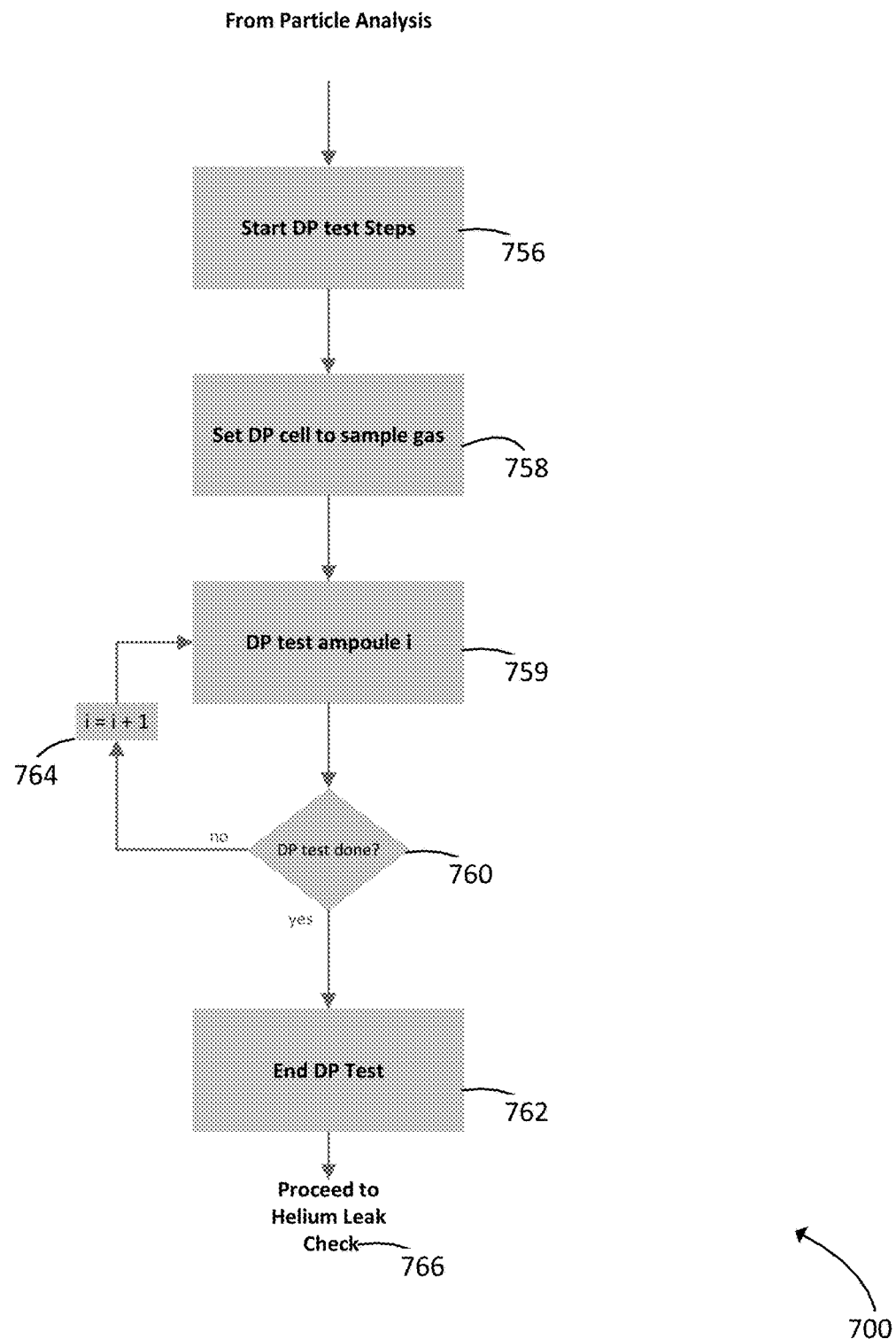
FIG. 7 is a flow chart of the ampoule differential pressure testing method according to an embodiment of the invention.

FIG. 7 shows a flow diagram for the Differential Pressure Testing process 700 according to an embodiment of the invention. Each ampoule is individually checked for differential pressure under a fixed condition of gas flow using a differential pressure cell 756. The ADACS is configured to place the DP Cell in fluid flow communication with an ampoule 758. This instrument measures the pressure drop of high purity inert gas flowing through each ampoule base or each ampoule bypass line with high sensitivity 759. High purity inert gas at a predetermined pressure, for example 0 psig, is passed through each ampoule, one at a time at a set flow rate. Preferably the flow rate is between 0.1 and 100 slpm. The differential pressure analysis is repeated for each ampoule, sequentially 764. Data for each ampoule are recorded automatically by the controller. When all ampoules have been tested, the differential analysis process ends 762 and the ampoules remain connected to the ADACS and are ready for the helium leak check process 766.

Ampoules that failed the tests for moisture, cleanliness, or differential pressure in the above steps may at this point be removed from ADACS for re-cleaning, re-drying, or re-work. Preferably, ampoules passing all the above quality tests remain in ADACS for helium leak checking.

Ampoule Leak Checking

Figure 8:
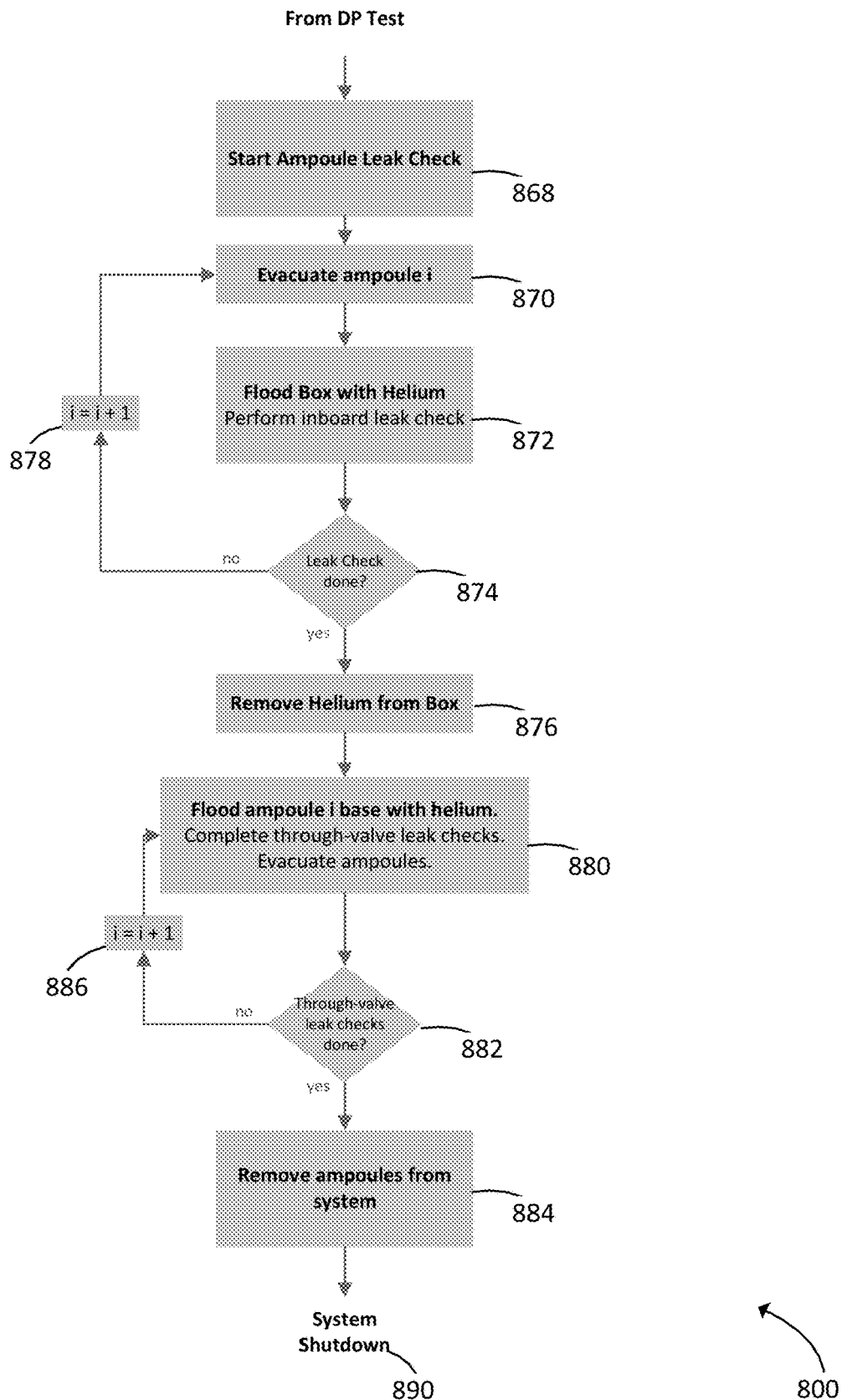
FIG. 8 is a flow chart of the ampoule leak testing method according to an embodiment of the invention.

FIG. 8 shows a flow diagram for the ampoule leak checking process 800 according to an embodiment of the invention. Ampoule heating during the drying process causes thermal expansion/contraction of connection points. The resulting stress in tubing and fittings may result in the development of coarse leaks. Vacuum decay checking is performed on each ampoule connection point, one at a time. The ADACS configures the helium leak detector station to be in fluid flow communication to the inlet port of a first ampoule 868. The ampoule inlet fitting is evacuated using the helium leak detector station 870. The ampoule outlet (vent) fittings are evacuated using the scroll-type vacuum pump. Vacuum at the connection points is then checked using electronic pressure transducers. Any coarse leaks in connection points that are detected are reported to the operators by the controller.

The ampoule box is flooded with helium to check for inboard leakage 872. A preferable mixture of gases in the environment surrounding the ampoules, and suitable for the leak testing, is at least 1% by volume of helium in air. The inboard leak check analysis is repeated for each ampoule, sequentially 878. Data for each ampoule are recorded automatically by the controller. When all ampoules have been tested, the inboard leak check analysis is complete.

The helium is then removed from the ampoule box using a clean dry air flush 876. An automated valve manipulator may be used to open/close manual ampoule valves during this programmed sequence. Automatic valves are opened/closed automatically by the controller. All test points are measured to a leak rate as small as $10^{-12}$ atm-cc/sec using a suitable helium leak detector station. Data for each ampoule are recorded automatically by the controller.

The ampoules are then checked for fine leaks using high purity helium gas 880. Leak checking is performed on each ampoule, one at a time. The test is repeated for each ampoule 886. High purity helium is introduced into the outlet (vent) line connection of the ampoules to check for proper sealing of closed ampoule manifold valves, one at a time. The checking process is performed in a programmed sequence. When all ampoules have been tested, the through-valve leak check process is complete 882.

The ampoules' bases are left under vacuum. The ampoules may then be removed from the ADACS 884 and the ADACS system is shut down 890. Faulty ampoules that failed the leak check are directed to a re-build process. Ampoules successfully passing all quality control tests by the ADACS are directed to re-use.

While the principles of the invention have been described above in connection with preferred embodiments, it is to be clearly understood that this description is made only by way of example and not as a limitation of the scope of the invention.

The invention claimed is:

1. A method for drying ampoules comprising:
    (a) creating an inlet connection and an outlet connection between an ampoule and a drying system, each of the inlet connection and the outlet connection providing fluid flow communication between the ampoule and the drying system;
    (b) drying the ampoule;
    (c) performing at least one test on the ampoule, the at least one test selected from the group consisting of a moisture test, a particle test, a differential pressure test, and an ampoule leak test;
    (d) collecting quality control data using at least one sensor for each of the at least one test performed in step (c);
    (e) performing steps (b) through (d) after step (a) and steps (c) and (d) after step (b); and
    (f) maintaining the inlet connection and outlet connection from step (a) through step (d).

2. The method of claim 1, further comprising:
    (g) placing the ampoule in a sealable chamber and performing steps (b) and (c) without removing the ampoule from the sealable chamber.

3. The method of claim 1, wherein the at least one test comprises at least two selected from the group consisting of a moisture test, a particle test, a differential pressure test, and an ampoule leak test.

4. The method of claim 1, wherein the at least one test comprises at least three selected from the group consisting of a moisture test, a particle test, a differential pressure test, and an ampoule leak test.

5. The method of claim 1, wherein step (b) further comprises:
   (b)(i) inserting the ampoule into an ampoule drying box;
   (b)(ii) providing the inlet connection in fluid flow communication with a source of heated purified purge gas;
   (b)(iii) purging the ampoule with the heated purified purge gas;
   (b)(iv) pressure cycling the heated purified purge gas; and
   (b)(v) heating the ampoule drying box.

6. The method of claim 5, wherein the ampoule drying box comprises a first zone and a second zone, the ampoule comprises at least one elastomeric valve seat and step (b)(v) further comprises heating the first zone to a first temperature and the second zone to a second temperature that is greater than the first temperature, wherein all of the elastomeric valve seat are located in the first zone.

7. The method of claim 5, wherein step (b) further comprises:
   (b)(vi) disconnecting the fluid flow communication between the inlet connection and the source of heated purified purge gas; and
   (b)(vii) placing the outlet connection in fluid flow communication with a vacuum pump;
   (b)(viii) placing the inlet connection in fluid flow communication with the source of heated purified purge gas;
   (b)(ix) performing step (b)(vi) simultaneously or after step (b)(v); and
   (b)(x) performing step (b)(viii) after step (b)(vii).

8. The method of claim 7, wherein step (b) further comprises:
   (b)(xi) performing steps (b)(vi) through (b)(viii) at least twice.

9. The method of claim 1, wherein the at least one test comprises the differential pressure test, the differential pressure test comprising the steps of:
   (c)(i) enabling fluid flow communication between an outlet port of the ampoule and a differential pressure test analyzer; and
   (c)(ii) measuring a differential pressure between the outlet port and a purified purge gas supply when the outlet port is in fluid flow communication with the purified purge gas supply.

10. The method of claim 1, wherein the at least one test comprises the ampoule leak test, the ampoule leak test comprising the steps of:
    (c)(i) placing an outlet port of the ampoule in fluid flow communication with a helium source;
    (c)(ii) placing an inlet port of the ampoule in fluid flow communication with a helium detector; and
    (c)(iii) measuring a helium leak rate using the helium detector while steps (c)(i) and (c)(ii) are being performed.

11. The method of claim 10, wherein the method further comprises inserting the ampoule into an ampoule dying box, and the ampoule leak test further comprises the step of:
    (c)(iv) flooding the ampoule drying box with helium to a concentration of at least 1 percent by volume of helium in air.

12. The method of claim 1, wherein the at least one test comprises the moisture test, the moisture test is performed using at least one moisture sensor and yields a detection level of 1.2 part per billion by volume or lower.

13. The method of claim 1, wherein the at least one test comprises the particle test, the particle test using at least one particle counter being sensitive to a plurality of micrometer-sized particles and utilizing a plurality of particle counter channels.

14. A drying system for ampoules comprising:
    a drying box adapted to provide a sealable internal volume, to selectively enable fluid flow communication with each of a source of heated, clean dry air and a box vent, and to accommodate an ampoule having an inlet port and an outlet port within the sealable internal volume;
    an inlet manifold comprising at least one inlet conduit and at least one inlet manifold valve that are adapted to selectively enable fluid flow communication between the inlet port and each of a helium leak detector and a source of purified purge gas having an in-line heater;
    an outlet manifold comprising at least one outlet conduit and at least one outlet manifold valve configured to selectively enable fluid flow communication between the outlet port and each of at least one quality control analyzer, a vacuum pump, a helium source, and an outlet vent;
    a quality control analyzer selected from the group consisting of a moisture analyzer, a particle analyzer, a differential pressure test analyzer and a helium leak check analyzer;
    at least one controller adapted to control the source of heated, clean dry air, the box vent, the source of purified purge gas, the in-line heater, the inlet manifold valve, the outlet manifold valve, the ampoule inlet port, the ampoule outlet port, the quality control analyzer, the vacuum pump, and the outlet vent.

15. The system of claim 14, wherein the at least one controller comprises executable code.

16. The system of claim 14, wherein the drying box further comprises a first heating zone and a second heating zone, each having a controllable heating element, wherein the at least one controller is adapted to heat the second heating zone to a higher temperature than the first heating zone.

17. The system of claim 16, wherein the first heating zone is located above the second heating zone.

18. The system of claim 14, wherein the quality control analyzer is a moisture analyzer capable of measuring moisture at a concentration of 1.2 part per billion by volume.

19. The system of claim 14, wherein the quality control analyzer is a particle analyzer comprising particle counters sensitive to a plurality of micrometer-sized particles and utilizing a plurality of particle counter channels.

* * * * *